United States Patent
Hall et al.

(10) Patent No.: US 6,644,878 B2
(45) Date of Patent: *Nov. 11, 2003

(54) FLUID-DISPENSING AND REFILLING SYSTEM FOR A POWER TOOTHBRUSH

(75) Inventors: Scott E. Hall, Kirkland, WA (US); James N. Larimer, Mercer Island, WA (US); Kevin Miller, Bellevue, WA (US); Richard Taylor, Fall City, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/993,122

(22) Filed: Nov. 5, 2001

(65) Prior Publication Data

US 2002/0081138 A1 Jun. 27, 2002

Related U.S. Application Data

(63) Continuation of application No. 09/229,979, filed on Jan. 13, 1999, now Pat. No. 6,402,410.

(51) Int. Cl.[7] .................................................. B43K 5/04
(52) U.S. Cl. ........................ 401/146; 401/149; 401/274; 401/286; 433/216
(58) Field of Search ................................ 401/146, 149, 401/150, 176, 179, 274, 286, 289; 15/22.1; 433/216; 417/211, 469; 92/162 R

(56) References Cited

U.S. PATENT DOCUMENTS

| | | | | |
|---|---|---|---|---|
| 4,692,047 A | * | 9/1987 | Endo | |
| 5,066,155 A | * | 11/1991 | English et al. | |
| 5,301,381 A | * | 4/1994 | Klupt | |
| 5,309,590 A | * | 5/1994 | Giuliani et al. | |

* cited by examiner

Primary Examiner—David J. Walczak
(74) Attorney, Agent, or Firm—Ernestine C. Bartlett

(57) ABSTRACT

The fluid delivery/refilling system includes a unit-of-use fluid reservoir for dentifrice or medication within a head portion of a power toothbrush, which is removable from the remainder thereof. A pump element is located in the brushhead and is configured so that the back and forth movement of the brushhead in operation results in fluid moving from the reservoir to a dispensing valve located in the brushhead. The dispensing valve has an end portion which is normally closed, opening under pressure of fluid from the pump. The refilling assembly is separate from the toothbrush and is configured to fit over the top of the toothbrush. Upward pressure exerted on the toothbrush when the toothbrush is within the refilling assembly results in movement of a core element in the refilling assembly, which in turn results in a hollow needle in the refilling assembly extending into a refiller valve in the head portion of the toothbrush. This results in a fluid path between the refilling assembly and the reservoir in the toothbrush. A selected sequence of movement of the toothbrush relative to the refilling results in fluid being moved from the external reservoir through the needle into the on-board unit-of-use reservoir in the toothbrush.

2 Claims, 6 Drawing Sheets

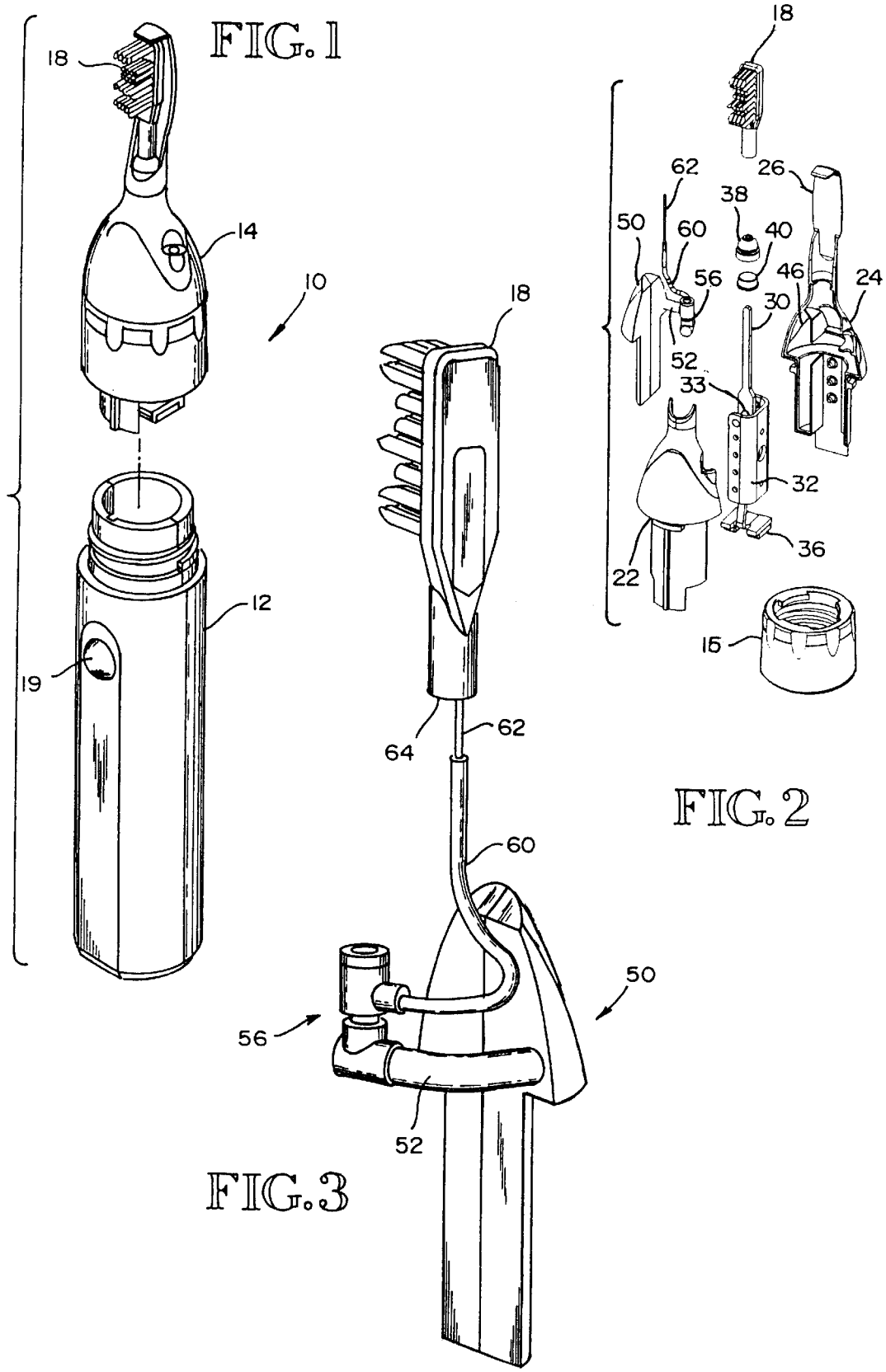

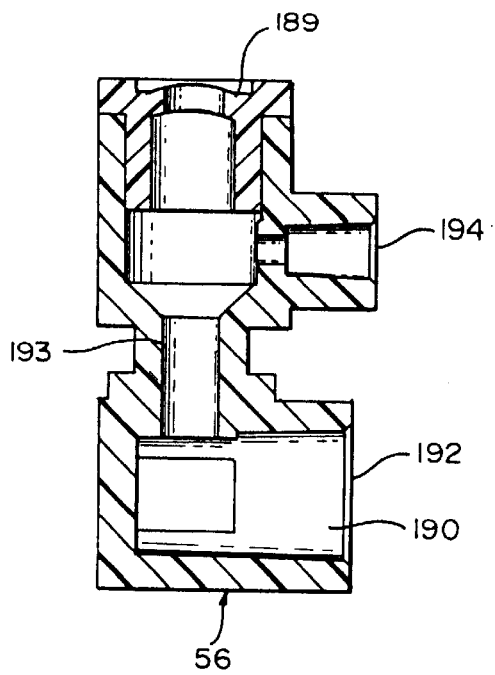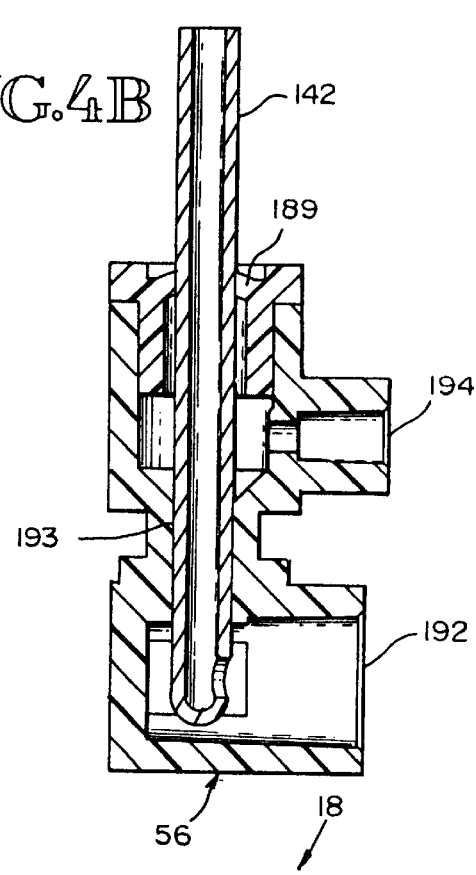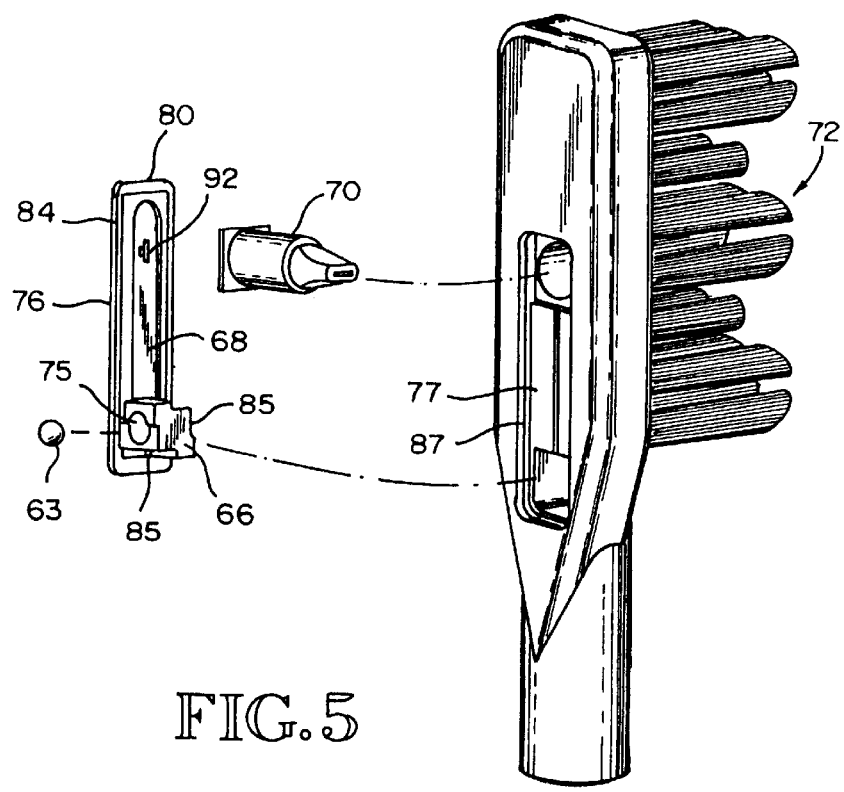

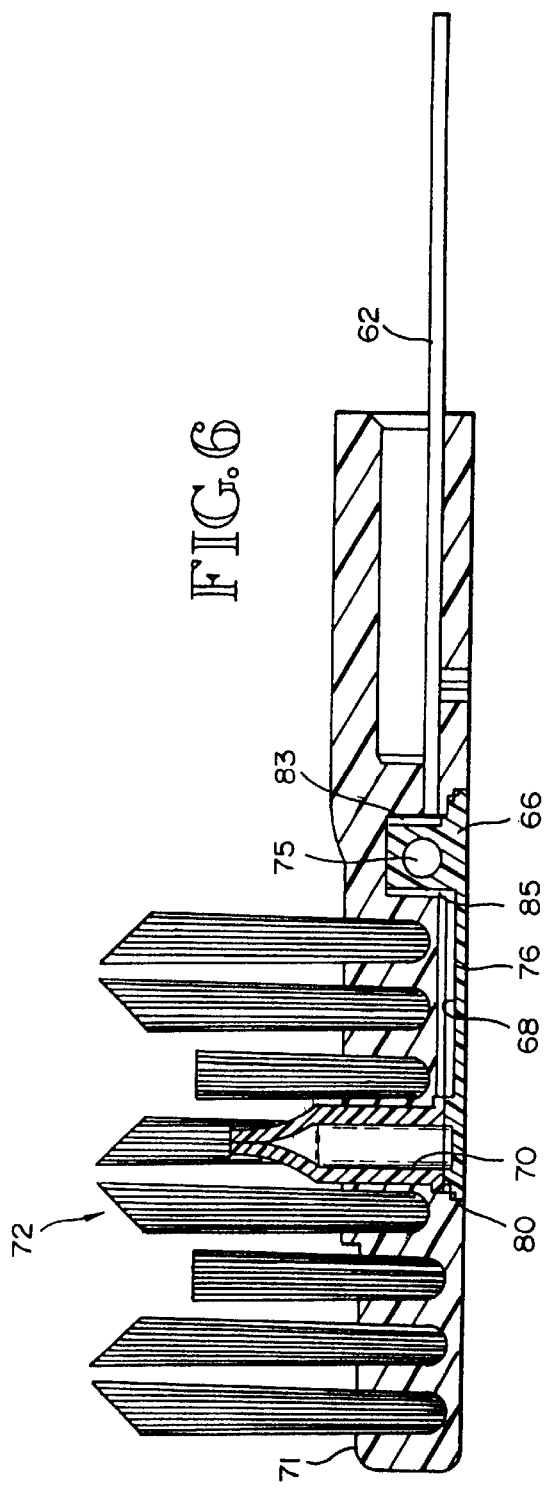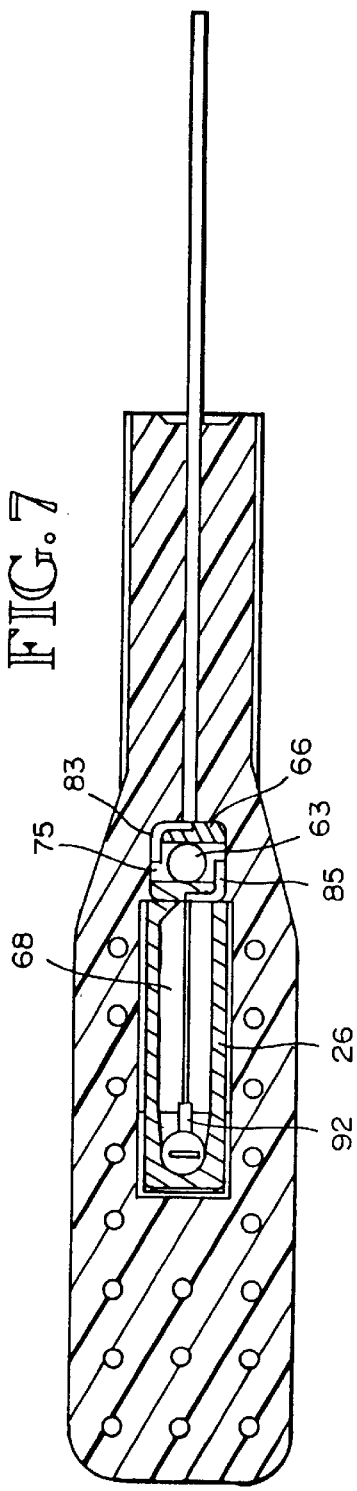

FLUID-DISPENSING AND REFILLING SYSTEM FOR A POWER TOOTHBRUSH

PRIOR APPLICATION

This is a continuation of prior patent application Ser. No. 09/229,979, now U.S. Pat. No. 6,402,410 filed on Jan. 13, 1999, titled "Fluid-Dispensing and Refilling System for a Power Toothbrush". Priority of that application is hereby claimed under 35 U.S.C. §120. The contents of that application are hereby incorporated by reference.

TECHNICAL FIELD

This invention relates generally to fluid-dispensing power toothbrushes, and more specifically concerns such a toothbrush which has an on-board reservoir and refilling arrangement and a fluid path arrangement which includes a pump element located in the brushhead portion of the toothbrush. The pump element uses the action of the moving brushhead to move fluid from the on-board reservoir to the bristles on the brushhead.

BACKGROUND OF THE INVENTION

The effective delivery of an oral dentifrice and/or medication capable of inhibiting or killing bacteria responsible for dental disease has long been desirable and has been the subject of a substantial amount of research effort. A wide variety of devices, both active and passive, have been developed to accomplish the delivery of dentifrice or medication to the bristles. Such devices have been developed for both manual and power toothbrushes. Manual toothbrushes typically use a hand-operated pump, such as shown in U.S. Pat. No. 4,221,492 to Boscardin et al and U.S. Pat. No. 4,413,370 to Gingras, while power toothbrushes use a variety of approaches, including on-board and external active pumping devices, which include various mechanical, pneumatic and hydraulic elements.

Some power toothbrush fluid-dispensing systems use the action of the toothbrush itself to draw a dentifrice from the reservoir to the bristles, such as shown in U.S. Pat. No. 5,309,590 to Giuliani et al. Some representative examples of fluid-dispensing systems for manual and power toothbrushes include U.S. Pat. No. 3,547,110 to Balamuth; U.S. Pat. No. 5,066,155 to English et al; U.S. Pat. No. 5,208,933 to Lustig and U.S. Pat. No. 5,062,728 to Kuo.

The reservoir for the dentifrice is typically located either in the handle portion of the toothbrush, such as shown in the '590 patent, or in a separate device, such as shown in the '110 patent. In some cases, the reservoir is disposable, so that when the fluid in the reservoir is depleted, the reservoir itself is discarded and a replacement reservoir is inserted. Such a system is shown in the '370 patent. In other systems, the reservoir is refillable. Typically, the reservoir contains sufficient fluid for a substantial number of individual uses of the fluid dentifrice or medication.

Various systems for dispensing the fluid from the brushhead are also known. In some cases, the fluid is dispensed from a plurality of openings in the brushhead itself, such as shown in the '492 patent, while in other cases, the fluid is dispensed through the bristles themselves, such as shown in U.S. Pat. No. 4,039,261 to Evans.

Fluid-dispensing systems in general, however, have often been difficult to operate, unreliable and expensive. Many such systems are too complex for reliable operation and/or are incapable of working properly, while other systems fail due to clogging of the fluid lines or exit openings, or poor pumping action, among other reasons. Also, it is difficult to design a system with a pump small enough to fit within a typical toothbrush structure. External pumps are often used, which are bulky and expensive. The pump element, whether on-board or external, is typically too complex for sustained, reliable operation, or too expensive to be practical. For all of these reasons, fluid-dispensing systems for both manual and power toothbrushes have not been particularly successful.

Because of the potential benefits, it is desirable to have a fluid-dispensing system in a power toothbrush which is reliable and yet sufficiently simple in design that it is practical to manufacture and maintain.

DISCLOSURE OF THE INVENTION

Accordingly, the present invention includes a fluid delivery system for a power toothbrush, comprising: a reservoir which is located within a toothbrush head portion of a power toothbrush, wherein the head portion is removable from the handle portion of the toothbrush; a pump member and associated fluid line for moving fluid from the reservoir to a brushhead part of the head portion of the toothbrush; and a dispensing member located in the brushhead, connected to the fluid line, for receiving fluid from the pump member and permitting exit of fluid therefrom to the vicinity of the bristles, under pressure provided by the pump member.

The invention also includes a pump for use in the fluid delivery system for a power toothbrush, comprising: a pump member for moving fluid from a reservoir to a dispensing member located in a brushhead portion of a toothbrush, wherein the pump member includes a chamber and a ball which moves within the chamber in response to movement of the brushhead during operation of the toothbrush, wherein movement of the ball in the chamber results in fluid moving from the reservoir into the pump member and then out of the pump member with sufficient pressure to move the fluid to the dispensing member and then outwardly therefrom.

The invention also includes a refilling system for a power toothbrush for use with a power toothbrush having an internal reservoir located therein from which fluid in operation is moved to the bristles in the brushhead, the internal reservoir having a small volume, at least one unit of use, the refilling system comprising: an external refilling assembly which is separate from the power toothbrush, the refilling assembly having a fluid reservoir which contains a substantial volume of fluid, at least a plurality of unit-of-use volumes of fluid; means associated with the refilling assembly and the power toothbrush for producing a fluid path from the refilling assembly to the power toothbrush; and means for moving fluid from the refilling assembly to the internal reservoir in the power toothbrush.

BRIEF DESCRIPTION OF THE DRAWINGS

FIG. 1 is a schematic view showing a toothbrush which incorporates the fluid-dispensing system of the present invention.

FIG. 2 is a partially exploded view of the head portion of the toothbrush of FIG. 1.

FIG. 3 is a schematic view showing a portion of the fluid-dispensing system of the present invention.

FIGS. 4A and 4B are cross-sectional views of a refill valve of the fluid-dispensing system of the present invention, with and without a refilling needle therein.

FIG. 5 is a partially exploded view showing the pump member and the brushhead.

FIGS. 6 and 7 are cross-sectional views showing the movement of fluid between the reservoir and the brushhead, including the pump element which moves the fluid.

BEST MODE FOR CARRYING OUT THE INVENTION

Figure 8:
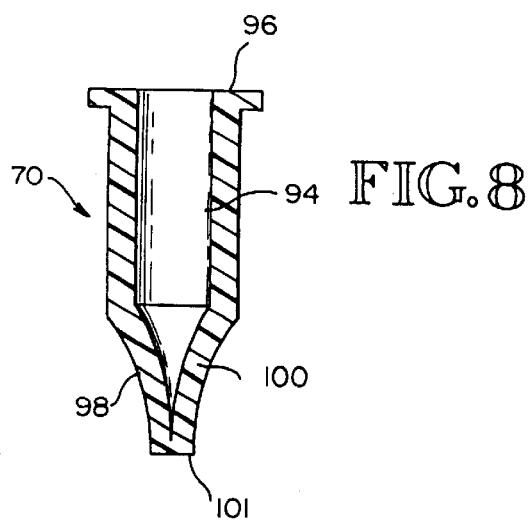
FIG. 8 is a cross-sectional view showing the dispensing valve of the fluid delivery system.

FIG. 1 shows a typical power toothbrush in which the fluid-dispensing and refilling system of the present invention is used. It should be emphasized, however, that the present invention is not limited to the particular power toothbrush shown and described or a particular brushhead movement. Rather, the principles of the present invention can be used with a variety of power toothbrush configurations and structural arrangements, with some aspects of the invention even being usable in a manual toothbrush.

The power toothbrush of FIG. 1, shown generally at 10, comprises a handle portion 12 and a removable head portion 14. In the handle portion is a power unit, including an electromagnetic driver and a battery for moving a brushhead 18, which is mounted on a pivoting arm, in a side-to-side manner, as discussed in more detail below. Toothbrush 10 is controlled by a pushbutton on/off switch 19.

FIG. 2 is an exploded view showing the principal parts of the head portion 14 of the toothbrush of FIG. 1. The head portion includes two mating body parts 22 and 24, which are fitted together about a support member 32. Body part 24 includes an extended shield 26 for brushhead 18. Brushhead 18 is mounted on a pivot arm 30, which in turn is mounted for pivoting action about a torsion pin pivot member 33, which extends between opposing sides of support member 32. Pivot arm 30 is driven by a electromagnetic driver (not shown) in handle portion 12 of the toothbrush, operating on magnetic elements 36 at the end of pivot arm 30. The structure and operation of such a toothbrush is described in more detail in U.S. Pat. No. 5,378,153 to Giuliani et al, owned by the same assignee as the present invention.

Rubber seal 38 and plastic ring 40 seal arm 30 to the body parts 22 and 24, preventing moisture from moving back into head portion 14. A nut portion 15 connects head portion 14 to handle portion 12 through a threaded connection. Positioned in an internal cavity 46 formed by the two mated body portions 22 and 24 is an on-board reservoir 50. On-board reservoir 50 is generally arrow-shaped in configuration, approximately 2 inches long, having front and rear similar flexible plastic panels joined together along the peripheral edges thereof. On-board reservoir 50 in the embodiment shown typically holds sufficient fluid for one brushing use, i.e. one "unit of use". This relatively small on-board reservoir volume is significant, in that it permits a fluid reservoir to be positioned in the removable head portion 14 of the toothbrush structure of FIG. 1. This arrangement has a number of advantages, including a relatively short fluid travel path and an overall simplicity of structure. Accordingly, when head portion 14 is replaced, such as when the bristles of brushhead 18 are worn, reservoir 50 as well as the associated fluid delivery system is part of the replacement unit.

Referring to FIGS. 2 and 3, extending from reservoir 50 is a short tube section 52 which fits into a lower end of a refilling valve 56, which is explained in more detail below. Extending from the side of refilling valve 56, above the entry point of tube section 52, is a flexible fluid line 60 which in the embodiment shown is flexible plastic material approximately 0.10 inches in diameter and approximately 1 inch long. Fluid line 60 connects to a fluid inlet tube 62, which has a diameter of approximately 0.05 inches, and extends into brushhead 18 at a proximal end 64 thereof.

FIGS. 5–8 show the fluid delivery structure within brushhead 18, including a fluid pump 66, a fluid-delivery cavity 68 which extends from pump 66 in a base element 76, and a fluid-dispensing valve 70 which extends upwardly from delivery cavity 68, through brushhead 18 above surface 71 of the brushhead, into the bristle region 72 of the toothbrush.

Fluid inlet tube 62 extends into brushhead 18 to where it contacts the entry region 83 (FIG. 7) of fluid pump 66. Fluid pump 66 is an irregular block of material having a cylindrical opening 75 which extends laterally thereof. Fluid pump 66 is positioned at one end of the elongated base element 76. Elongated base element 76 is approximately 0.03 inches thick and has a cutout or cavity portion 68 which extends from pump 66 to approximately the other end 80 of base element 76. Cavity portion 68 in the embodiment shown is approximately 0.015 inches deep.

As shown in FIG. 5, fluid pump 66 and base element 76 in the embodiment shown form a unitary member, which fits into a matching cavity 77 in the lower surface of the brushhead. Cavity 77 is configured to provide a solid seal for the ends of cylindrical opening 75 in pump 66 when the unitary member is correctly positioned in cavity 77. Fluid delivery cavity 68 connects exit portion 85 of pump 66 and the lower end of dispensing valve 70. A lip 84 surrounding cavity 68 in base element 76 contacts a mating surface 87 in the brushhead when the unitary pump and base element are in place, providing a fluid-tight seal around cavity 68. Cavity 68 thus serves as a fluid-delivery means connecting pump 66 with dispensing valve 70.

Pump 66 is configured with opposing corners being relieved, the relieved portions extending, respectively, from the opposing open ends of cylindrical opening 75, around adjacent corners of the block, to a point approximately half-way along the adjacent side of the pump 66. This configuration is shown most clearly in FIGS. 6 and 7. A spherical ball 63, which functions as a piston, rides in cylindrical opening 75. Entry region 83 overlaps one end of opening 75, while exit region 85 overlaps the other end of opening 75. Exit region 85 connects to fluid delivery cavity 68 in the base element. Hence, there is a complete fluid path from tube 62 to cavity 68. The ball 63 moves within cylindrical opening 75, producing a pumping action for the fluid which enters opening 75, as the brushhead moves from side to side in operation.

Proper clearance between ball 63 and the interior surface of cylindrical opening 75 is important for correct pumping operation, with adequate fluid pressure to valve 70. In the embodiment shown, the clearance is approximately 0.0015 inches.

In operation, during the outlet stroke, as the ball moves toward the exit or outlet region 85 for opening 75, fluid is moved both toward the outlet region and also around the piston toward the inlet region 83 for opening 75. On the return stroke of the piston (toward the inlet region 83), the closed dispensing valve forces fluid to pass around the ball toward the outlet region, in preparation for the next outlet stroke. The flow rate is partially dependent on the amplitude of the brushhead movement and hence is a function of the loading of the toothbrush. When the brushhead system is a resonant system, such as described in the '153 patent, the flow rate increases when the bristles are in contact with the teeth. The pumping action will occur with or without a dispensing valve at the end of the fluid path and is self-priming in operation, i.e. it can pump air.

The action of the piston ball 63 moving back and forth in the opening due to the back and forth action of the brushhead forces fluid out of the outlet region 85 of the pump and allows fluid to enter inlet region 83 from fluid tube 62. In the outlet region 85, fluid moves around the corner of the pump block and along the adjacent side, bound by the walls of the brushhead cavity into which the pump and base element fits. The fluid moves into cavity 68 in base element 76, around a small diverting member 92 near the end of cavity 68 into internal opening 94 of base portion 96 of the dispensing valve 70.

The dispensing valve 70 is shown in FIG. 8. Internal opening 94 is approximately 0.07 inches in diameter. Valve 70 in the embodiment shown is 0.34 inches high. Valve 70 is known as a "duck bill" valve because it has two converging lip portions 98 and 100 at the free end 101 thereof. The two lip portions 98 and 100 are normally closed, i.e. pressed together, to prevent leakage and/or backflow of fluid. Fluid is moved by the back and forth action of the brushhead and the action of the pump, into valve 70, with sufficient pressure to force apart the two lips 98 and 100, dispensing the fluid into the area of the bristles in spurts on each "outlet" stroke of the piston. The valve shown not only prevents backflow of fluid, which is a potential source of contamination, but also assists in making the pump self-priming as well as determining the output flow speed and velocity.

The "duck bill" valve 70 is conventional, made out of a flexible plastic material to facilitate opening and closure of the lip portions 98 and 100. In the embodiment shown, the free end of valve 70 extends above the base of the brushhead approximately 0.18 inches. It is located approximately in the middle of the bristles both longitudinally and laterally, although this is not necessary to proper operation of the system.

In operation, as brushhead 18 moves from side to side, such that piston ball 63 moves back and forth between the inlet and outlet ends of the cylindrical opening 75, small volumes (approximately 0.00013 cc) of fluid will be successively moved from the reservoir through the pump 66 and then to the dispensing valve 70. The lips 98, 100 of valve 70 part slightly with each small surge of fluid, but close again after the surge has passed. The successive amounts of fluid are forced out into the bristle area and are delivered to the desired region of the teeth by the action of the moving bristles.

Hence, there is a continuous (in small successive spurts) delivery of fluid to the area of the bristles during bristle action. This system has several advantages over existing systems. First, the continuous (in the form of successive spurts or pulses) nature of the fluid delivery prevents the effect of the fluid from becoming diluted over the brushing time, which is the case when the fluid, be it conventional dentifrice or oral medication, is administered at the start of brushing. Second, the effect of the fluid is enhanced with the present invention because the fluid can be provided directly to the area of bristle action.

In the case of the particular action of the toothbrush shown, in the manner and with the operating characteristics, including frequency and amplitude, set forth in the '590 patent, the effect of the fluid, dentifrice or medication, is frequently enhanced due to the cavitation and other action of the fluid created by the bristle action. This is in addition to the precise delivery of the fluid to specific regions of interest in the mouth, including the gingival areas in the gum line and between the teeth.

Hence, the fluid-dispensing system of the present invention is not only practical and reliable, but it has a significant therapeutic effect when used under selected operating conditions, such as those produced by the action of the toothbrush in the '590 patent.

As indicated above, reservoir 50 in the embodiment shown has a unit-of-use volume, i.e. the volume is sufficient for one brushing of typical length, i.e. two minutes or so. The system of the present invention also includes a refilling system for the unit-of-use reservoir. The refilling system is shown in FIGS. 9–14.

Figure 9:
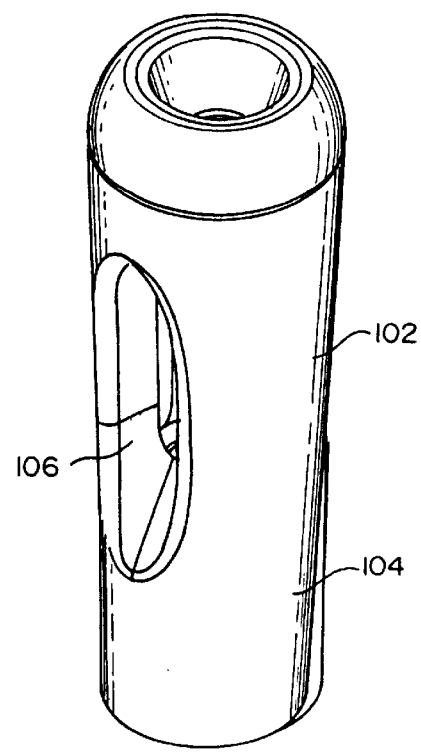
FIGS. 9 through 13 are diagrams showing the refilling assembly of the present invention and the process of refilling the on-board reservoir of the toothbrush of FIG. 1.

FIG. 9 shows the refiller apparatus 102 in general, for use with the toothbrush of FIG. 1. To refill the unit-of-use reservoir 50 in the head portion of the toothbrush, the refiller apparatus 102 fits down over the top of the toothbrush, with the head portion and the brushhead portion of the toothbrush extending up into the interior of the refiller apparatus 102. The refiller apparatus includes a housing 104, with a viewing window 106 which shows a portion of the interior of the refiller apparatus so that the user can ascertain proper insertion of the toothbrush.

Figure 10:
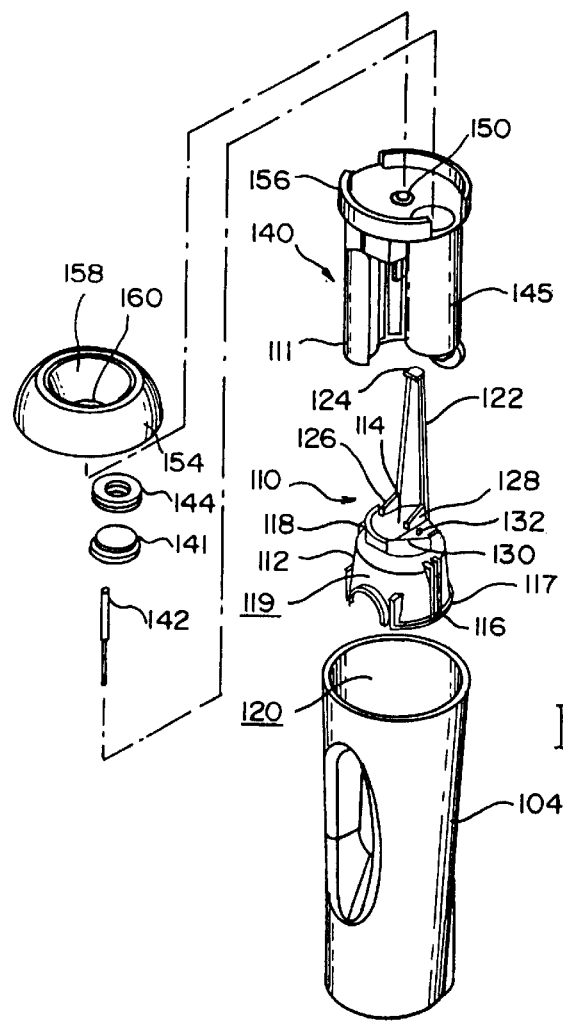

FIG. 10 shows the various portions of the refiller apparatus. It includes housing 104 and an interior core element 110. Core element 110 includes a lower portion 112 which is configured to receive and mate with an upper part of the head portion of the toothbrush. Brushhead 18 extends upwardly through an opening 114 in core element 110. Core element 110 has opposing side tracks 116 and 118 which extend from a lower edge 117 of the core element upwardly thereof, on the exterior surface 119 thereof. Tracks 116 and 118 mate with corresponding mating channels (not shown) on interior surface 120 of housing 104.

This arrangement permits the core element 110 to move up and down a selected distance within housing 104 in a reliable fashion, without rotation or side-to-side movement. Extending upwardly from the top of lower portion 112 of core element 110 is a narrow extending member 122, with a horizontal lip 124 at the upper end thereof and two spaced wing elements 126 and 128 at the base thereof, adjacent the top of the lower portion. Lower portion 112 of core element 110 also includes a flat surface portion 130 at the upper end thereof, adjacent wing element 128. Extending through this flat surface portion 130 is a small opening 132. Opening 132 conveniently and readily accommodates a refilling needle from the refilling apparatus.

Positioned above core element 110 is a pump assembly 140, which includes therein a refilling reservoir 111. Positioned within pump assembly 140 is a fill needle 142, which is oriented vertically with a base portion 141 of the needle mounted to a seal assembly 144, which fits into a pump chamber portion 145 of the pump assembly 140 in a sealing relationship to the interior peripheral surface of the pump chamber. In the top of the pump assembly 140 is an opening 150 which connects with refilling reservoir 111 within the pump assembly. A top element 154 snaps onto an upper lip 156 of pump assembly 140. At the center of top element 154 is a cavity-like portion 158, at the bottom of which is an opening 160 (shown partially in FIG. 10), which can be either in or out of registry with opening 150 in the pump assembly, depending upon the rotational position of the top element. The refiller reservoir 111 may be filled through these two openings 160 and 150 when the top element is in the correct position such that the two openings are in registry.

Figures 11, 12:
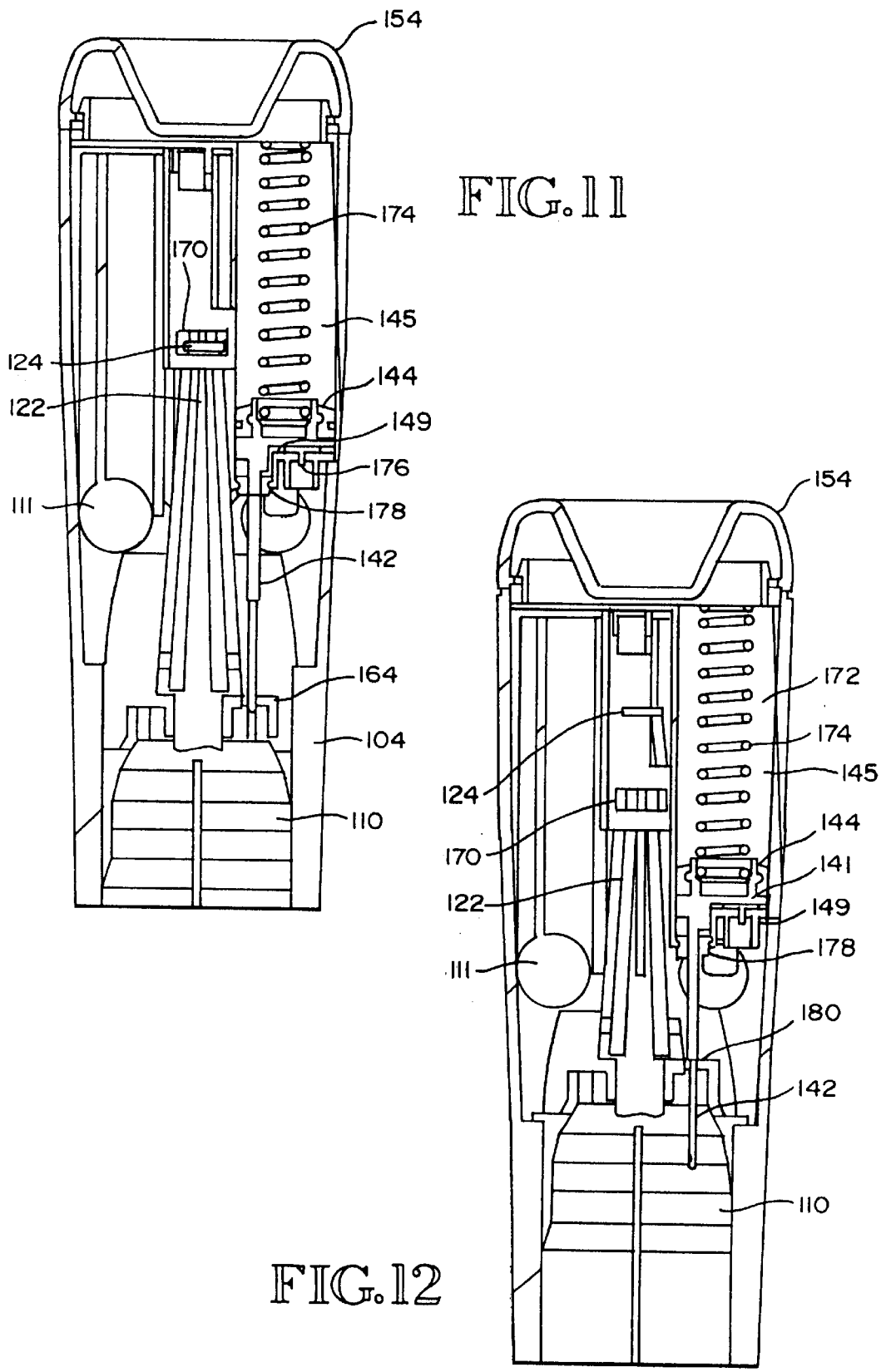
Figure 13:
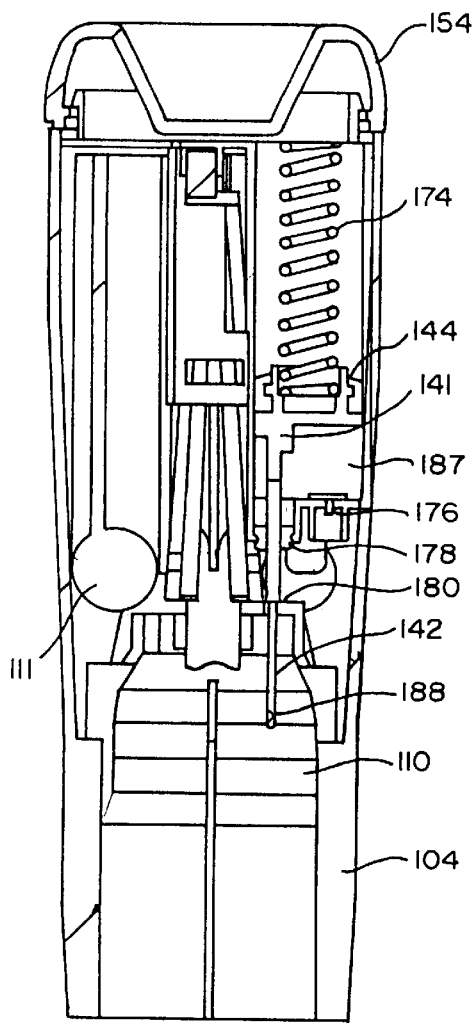
Figure 14:
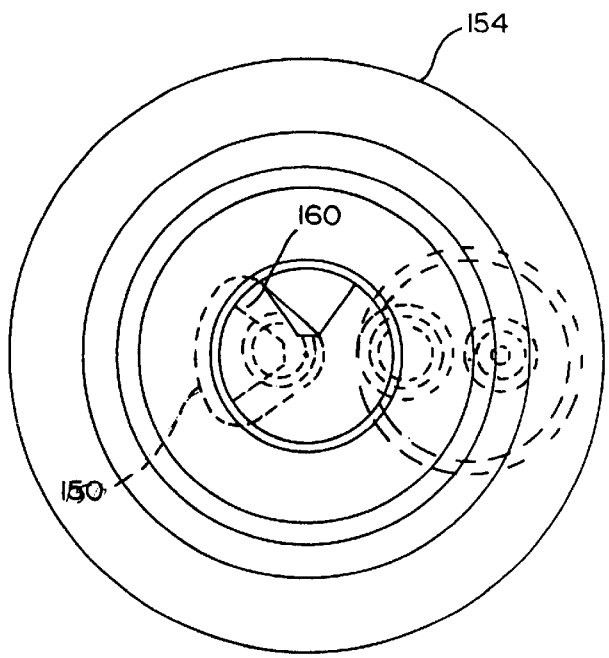
FIG. 14 is a top plan view of the refilling assembly.

FIGS. 11–13 are cross-sectional diagrams showing the sequence of steps in the refilling process for the unit-of-use reservoir 50 in the toothbrush. In FIG. 11, the toothbrush has been just positioned within the refiller apparatus, with the core element 110 being at its lowermost position. In this position, lip 124 of extending member 122 remains in a receiving slot 170 within the refiller apparatus, as is the case when there is no toothbrush within the refiller. In this position, the lower end 164 of fill needle 142 just penetrates through opening 132 in surface 130 of the core element. The needle base 141 and seal assembly 144 are in their lowermost position within pump chamber 145. A spring 174 within pump chamber 145 tends to maintain the needle base and seal assembly in their lowermost position. Chamber inlet valve 176 at the lower end of pump chamber 144 is in its closed (lowered) position, as shown. The body of needle 142 is sealed to the lower edge member 149 of chamber 145 by seal 178.

As the toothbrush is inserted further into core element 110 by a user, the particularly configured curved shoulders of the head portion of the toothbrush push against the wing elements 126, 128 at the base of extending member 122 (FIG. 10). This action forces the extending member 122 backwardly sufficiently that lip 124 at the top of the extending member moves out of receiving slot 170, allowing the core member to move further up within the refiller apparatus. Further upward pressure on the toothbrush by the user results in further upward movement of the core element 110, with fill needle 142 penetrating further through opening 132 in the core element and into refiller valve 56 of the head portion 14 of the toothbrush (shown in FIG. 2).

FIG. 12 shows a mid-position of the movement of the core element where the upper surface of the core element 110 abuts a shoulder portion 180 of fill needle 142. To achieve this mid-position, the core element has moved upwardly within the refilling apparatus, but neither the needle itself nor the seal assembly 144 to which base 141 of fill needle 142 is attached has moved within pump chamber 145. Inlet valve 176 remains closed.

Referring now to FIG. 13, further upward movement of the toothbrush will result in further upward movement of core element 110 within the refilling assembly, the core element pushing upwardly against the shoulder portion 180 of fill needle 142. The needle 142, its base section 141 and the seal assembly 144 move upwardly within pump chamber 145, against the action of spring 174, producing a volume 187 between the needle base 141 and the lower end of pump chamber 145. Fluid from the refilling reservoir is drawn into volume 187 by vacuum action through inlet valve 176, which moves upwardly. Volume 187 fills with fluid as needle base 141 and seal assembly 144 move upwardly against the action of spring 174 in pump chamber 145.

Fill needle 142 has spaced openings around its periphery where it joins base portion 141. More particularly, needle 142 joins base portion 141 through a "cross-hair" structure, with the space between the adjacent portions of the cross-hair structure being open to the hollow interior of the needle. When the core element reaches its highest position within the refiller assembly, volume 187 has a capacity of approximately 4 ml, and is completely filled with fluid from the refilling reservoir 111.

At this point, the brushhead is withdrawn slightly. When the brush is withdrawn, the action of spring 174 forces the seal assembly 144, the base portion 141 of the needle and the fill needle 142 itself downwardly with pump chamber 145, decreasing the volume 187. The fluid in volume 187 is forced through the cross-hair openings at the base of the fill needle down into and through the hollow interior of fill needle 142 and out opening 188 at the lower end of the needle.

Opening 188 in needle 142 at this point is within the refilling valve in the toothbrush, as explained above. Referring to FIGS. 4A and 4B, needle 142 extends down through a top seal element 189 in the valve 56 to approximately the lower end 190 thereof. The valve 56 seals around the needle 142 in region 193, preventing any backflow of fluid from the needle through outlet port 194, which connects with fluid line 60. Fluid coming out opening 188 in the needle moves through port 192 into fluid line 52 (FIG. 3), which leads to the on-board reservoir 50.

The amount of fluid moved from the refilling apparatus into reservoir 50 is approximately 4 milliliters in the embodiment shown, which is the amount of fluid appropriate for one unit-of-use. Other amounts, however, could be dispensed to the on-board reservoir, if desired, depending on the capacity of the reservoir. When the toothbrush is sufficiently withdrawn from the refilling assembly, the needle, its base portion and the seal assembly are back to their original position in the refilling apparatus, as shown in FIG. 12. The toothbrush is then removed from the refiller apparatus, ready for a single use of fluid, i.e. a single brushing event. The refilling of the on-board reservoir 50 occurs prior to each brushing.

While the embodiment shown includes a single unit-of-use reservoir, with the reservoir being filled for each brushing, it is possible to modify the reservoir so as to have fluid for more than one use. The external refilling assembly, however, will still be useful for convenient refilling of the reservoir, permitting use of a relatively small fluid reservoir on board the toothbrush, thus saving space and pumping requirements.

Hence, a new fluid-dispensing and refilling system for power toothbrushes has been described. The system includes a small unit-of-use reservoir in a removable head portion of the toothbrush. A fluid line extends from the reservoir to a small pump element located in the brushhead. The pump element, with the back and forth action of the brushhead, provides movement of the fluid from the reservoir to a dispensing valve in the head of the toothbrush, through which fluid moves to the bristles.

The on-board reservoir is refilled before each use by a separate refilling apparatus, into which the toothbrush is inserted. Movement of the brushhead relative to the refilling apparatus in a particular sequence results in fluid in the refiller reservoir moving through a fill needle and refiller valve in the head portion of the toothbrush into the on-board unit-of-use reservoir.

Although a preferred embodiment of the invention has been disclosed herein for illustration, it should be understood that various changes, modifications and substitutions may be incorporated in such embodiment without departing from the spirit of the invention, which is defined by the claims as follows.

What is claimed is:

1. A fluid delivery system for a power toothbrush, the power toothbrush including a brushhead part having bristles located thereon for cleaning of teeth, comprising:
 a fluid reservoir adapted to be located within the power toothbrush, the reservoir having a fluid volume capacity to accommodate approximately only a single unit-of-use for only one brushing event of typical time length, approximately a maximum of 4 ml of fluid;
 a pump member and associated fluid line for moving fluid from said reservoir to the brushhead part of the power toothbrush, wherein the pump member includes a chamber and a ball which moves within the chamber in response to the movement of the brushhead in operation of the toothbrush, wherein movement of the ball results in fluid moving from the reservoir into the pump member and then from the pump member to the dispensing member in the brushhead; and a dispensing member adapted to be located in the brushhead part of the power toothbrush connected to said fluid line, permitting exit of fluid to the vicinity of the bristles, under pressure provided by the pump member.

2. A fluid delivery system for a power toothbrush, the power toothbrush including a head portion which includes a brushhead part having bristles located thereon for cleaning of the teeth and a handle portion which includes therein a drive assembly for the brushhead, comprising:

a fluid reservoir adapted to be located within the head portion, the reservoir having a fluid volume capacity to accommodate approximately only a single unit-of-use for only one brushing event of typical time length, approximately a maximum of 4ml of fluid;

a pump member and associated fluid line for moving the fluid from said reservoir to the brushhead part of the power toothbrush;

a dispensing member adapted to be located in the brushhead part of the power toothbrush connected to said fluid line, permitting exit of fluid to the vicinity of the bristles, under pressure provided by the pump member; and a fluid refilling line connected to an interior of the fluid reservoir and a fluid valve associated with the refilling line which, when open, permits the reservoir to be refilled for each successive use of the toothbrush, wherein the head portion is removable from the handle portion, along with the fluid reservoir, the pump member and associated fluid line, the dispensing member and the refilling line and valve.

* * * * *